(12) United States Patent
Park et al.

(10) Patent No.: US 10,898,149 B2
(45) Date of Patent: Jan. 26, 2021

(54) STANDARDIZING BREAST DENSITY ASSESSMENTS

(71) Applicant: International Business Machines Corporation, Armonk, NY (US)

(72) Inventors: Sun Young Park, San Diego, CA (US); Dusty Sargent, San Diego, CA (US)

(73) Assignee: International Business Machines Corporation, Armonk, NY (US)

( * ) Notice: Subject to any disclaimer, the term of this patent is extended or adjusted under 35 U.S.C. 154(b) by 78 days.

(21) Appl. No.: 16/216,052

(22) Filed: Dec. 11, 2018

(65) Prior Publication Data

US 2020/0178918 A1 Jun. 11, 2020

(51) Int. Cl.
| | |
|---|---|
| *A61B 6/00* | (2006.01) |
| *G06T 7/00* | (2017.01) |
| *A61B 5/00* | (2006.01) |

(52) U.S. Cl.
CPC .......... *A61B 6/502* (2013.01); *A61B 6/5217* (2013.01); *G06T 7/0014* (2013.01); *A61B 5/4312* (2013.01);

(Continued)

(58) Field of Classification Search
CPC ..... A61B 6/502; A61B 6/5217; A61B 5/4312; A61B 6/5205; A61B 6/461; A61B 5/7267;

(Continued)

(56) References Cited

U.S. PATENT DOCUMENTS 7,664,604 B1 * 2/2010 Heine .................... G16H 50/30
702/19
8,296,247 B2 10/2012 Zhang et al.
(Continued)

FOREIGN PATENT DOCUMENTS

WO 2002015113 A2 2/2002
WO 2017223560 A1 12/2017

OTHER PUBLICATIONS

Ayer et al., "Breast Cancer Risk Estimation with Artificial Neural Networks Revisited: Discrimination and Calibration," Cancer, vol. 116, No. 14, Jul. 15, 2010, pp. 3310-3321.

(Continued)

*Primary Examiner* — Nimesh Patel
(74) *Attorney, Agent, or Firm* — Robert A. Voigt, Jr.; Wintead PC

(57) ABSTRACT

A method, system and computer program product for determining changes in breast density. A generative adversarial network is trained to predict an appearance of a mammogram image for a patient's current examination based on mammogram images assigned labels of a first type of density classification. An appearance of a mammogram image for a patient's current examination is predicted using the generative adversarial network based on a mammogram image(s) obtained from the patient's prior examination assigned labels of the first type of density classification. A comparison is made between the predicted and actual mammogram images for the patient's current examination to determine if there is a difference between scores assigned to the predicted and actual mammogram images, and if so, whether such difference can be attributed to the subjective assessment by different physicians or changes in the standards of density classification or is due to a real change in breast density.

18 Claims, 4 Drawing Sheets

(52) U.S. Cl.
CPC ... *A61B 6/5205* (2013.01); *G06T 2207/10116* (2013.01); *G06T 2207/30068* (2013.01)

(58) Field of Classification Search
CPC ..... A61B 6/466; A61B 8/0825; A61B 5/7475; A61B 6/465; A61B 6/5211; A61B 10/0041; A61B 2034/107; A61B 2090/367; A61B 34/10; A61B 5/0022; A61B 5/7264; A61B 5/7485; A61B 6/563; A61B 2576/00; A61B 2576/02; A61B 5/708; A61B 5/743; A61B 6/00; A61B 6/03; A61B 8/406; A61B 8/5223; A61B 6/0414; A61B 5/0013; A61B 5/002; A61B 8/085; A61B 8/0858; A61B 6/482; A61B 8/565; G06T 7/0014; G06T 2207/30068; G06T 2207/10116; G06T 2207/20081; G06T 7/0012; G06T 2207/20084; G06T 2207/30096; G06T 7/11; G06T 2207/10081; G06T 2207/10132; G06T 2207/20021; G06T 15/08; G06T 2200/04; G06T 19/20; G06T 2200/24; G06T 17/00; G06T 2207/10136; G06T 2207/30004; G06T 3/4046; G06T 5/002; G06T 7/77; G06T 2207/10004; G06T 2207/20104; G06T 7/41; G06T 11/005; G06T 2207/20172; G06T 2210/41; G06T 5/009; G06T 5/20; G06T 7/10; G06T 7/44; G06T 2207/20221; G06N 3/0454; G06N 3/08; G06N 20/00; G06N 3/00; G06N 3/02; G06N 3/0472; G06N 3/082; G06N 5/022; G06K 2209/05; G06K 9/4628; G06K 9/6277; G06K 9/628; G06K 9/3233; G06K 9/623; G06K 9/6256; G06K 9/6267; G06K 9/00201; G06K 9/00617; G06K 9/0063; G06K 9/2054; G06K 9/3241; G06K 9/42; G06K 9/52; G06K 9/6223; G06K 9/46; G06K 9/6254; G06K 9/66; G06K 9/6276; G06K 9/6226; G06K 9/6262; G06F 3/0481; G06F 3/147; G06F 17/18; G06F 19/321; G06F 16/285; G06F 17/175; G06F 3/04842; G06F 3/04847; G16H 50/70; G16H 50/30; G16H 30/40; G16H 15/00; G16H 50/20; G16H 40/63; G16H 50/50; G16H 30/20; C12Q 1/6886; C12Q 2600/158; C12Q 2600/112; C12Q 2600/118; C12Q 2600/154; C12Q 2600/178

See application file for complete search history.

(56) References Cited

U.S. PATENT DOCUMENTS

| | | |
|---|---|---|
| 9,895,121 B2 | 2/2018 | Abdolell et al. |
| 2009/0093711 A1* | 4/2009 | Hermosillo Valadez ................... G16H 30/40 600/420 |
| 2015/0079566 A1* | 3/2015 | Salkowski ........... G09B 23/286 434/262 |
| 2017/0200268 A1* | 7/2017 | Podilchuk ............ G06K 9/6232 |
| 2017/0202530 A1* | 7/2017 | Mainprize ............. A61B 6/469 |
| 2019/0090834 A1* | 3/2019 | Pauly .................... G06T 7/0012 |
| 2019/0172581 A1* | 6/2019 | Zlotnick ................ G06N 20/10 |
| 2019/0287685 A1* | 9/2019 | Wu ....................... G06K 9/6279 |
| 2020/0082282 A1* | 3/2020 | Simpson .............. G06N 3/0454 |

OTHER PUBLICATIONS

Baker et al., "Breast Cancer: Prediction with Artificial Neural Network Based on BI-RADS Standardized Lexicon," Radiology, vol. 196, No. 3, Sep. 1995, pp. 817-822.

Kim et al., "ICADx: Interpretable Computer Aided Diagnosis of Breast Masses," https://arxiv.org/abs/1805.08960, Submitted on May 23, 2018, pp. 1-10.

Li et al., "Computer-Aided Assessment of Breast Density: Comparison of Supervised Deep Learning and Feature-Based Statistical Learning," Physics in Medicine & Biology, vol. 63, 2018, pp. 1-15.

Mohamed et al., "A Deep Learning for Classifying Breast Density Categories," Medical Physics, vol. 45, No. 1, Jan. 2018, pp. 314-321.

Moya et al., "Multi-Category Classification of Mammograms by Using Convolutional Neural Networks," 2017 International Conference on Information Systems and Computer Science (INCISCOS), Quito, 2017, pp. 133-140.

Wollmann et al., "Adversarial Domain Adaptation to Improve Automatic Breast Cancer Grading in Lymph Nodes," 2018 IEEE 15th International Symposium on Biomedical Imaging (ISBI 2018), Washington, DC, Apr. 4-7, 2018, pp. 582-585.

Wu et al., "Breast Density Classification with Deep Convolutional Neural Networks," https://arxiv.org/abs/1711.03674, Submitted on Nov. 10, 2017, pp. 1-5.

* cited by examiner

STANDARDIZING BREAST DENSITY ASSESSMENTS

TECHNICAL FIELD

The present invention relates generally to mammography, and more particularly to standardizing breast density assessments.

BACKGROUND

Mammography (also called mastography) is the process of using low-energy X-rays (usually around 30 kVp) to examine the human breast for diagnosis and screening. The goal of mammography is the early detection of breast cancer, typically through detection of characteristic masses or microcalcifications. As with all X-rays, mammograms use doses of ionizing radiation to create images. These images are then analyzed for abnormal findings.

Currently, mammogram images are analyzed to determine breast density since women whose breasts appear dense on the mammogram image have a higher risk for breast cancer, including some aggressive breast cancers. One of the strongest known risk factors for breast cancer is high breast density—that is, relatively little fat in the breast and more connective and glandular tissue, as seen on the mammogram image.

Breast density in mammogram images is currently analyzed by a radiologist using a standard referred to as the Breast Imaging-Reporting and Data System (BI-RADS) standard. BI-RADS is a quality assurance tool designed to standardize reporting and is used by medical professionals to communicate a patient's risk of developing breast cancer. BI-RADS includes standardized numerical codes that are typically assigned by a radiologist after interpreting a mammogram image, which are included in a report (breast imaging report) concerning the patient's risk of developing breast cancer.

There have been several updates to the BI-RADS standard. For example, the BI-RADS is currently on its fifth edition, which was released in February of 2014. Some of the changes from the fourth edition to the fifth edition include the categorization of breast density.

In the fourth edition of the BI-RADS standard, breast density is characterized on the basis of the percentile of glandular tissue within each breast (<25%, 25%-50%, 51%-75%, or >75%). Breast density characterization in the fifth edition is purely subjective, with elimination of the percentiles. The fifth edition reverts to the original description of breast density that was used in the first few editions. The four category descriptors are phrased the same in the fourth and fifth editions: almost entirely fatty, scattered areas of fibroglandular density, heterogeneously dense, and extremely dense. As a result of the continuous changes to the BI-RADS standard, radiologist reports may include different breast density characterizations.

Additionally, along with changes to the BI-RADS standard, the radiologist report concerning the patient's risk of developing breast cancer may provide descriptions of breast density that do not follow any of the BI-RADS standards.

As a result of the continuous changes to the BI-RADS standard as well as radiologist reports that provide descriptions of breast density that may not follow any of the BI-RADS standards, it may be difficult to assess the patient's risk for breast cancer based on the patient's medical history. Additionally, there may be difficultly in evaluating the changes in breast density for a patient over time.

SUMMARY

In one embodiment of the present invention, a method for standardizing breast density classifications in mammogram images comprises receiving a set of mammogram images labeled by users with a first type of breast density classification. The method further comprises training a convolutional neural network to predict labels of the first type of breast density classification in mammogram images using the received set of mammogram images. The method additionally comprises assigning labels of the first type of breast density classification to mammogram images labeled under a second type of breast density classification using the convolutional neural network.

Other forms of the embodiment of the method described above are in a system and in a computer program product.

In another embodiment of the present invention, a method for determining changes in breast density in mammogram images comprises receiving a set of mammogram images labeled by users with a second type of breast density classification, where the mammogram images comprise mammogram images of patients obtained from both prior and current examinations. The method further comprises assigning labels of a first type of breast density classification to the received set of mammogram images using a convolutional neural network trained to predict labels of the first type of breast density classification in mammogram images. The method additionally comprises training a generative adversarial network to predict an appearance of a mammogram image for a patient's current examination based on the received set of mammogram images assigned labels of the first type of breast density classification. Furthermore, the method comprises predicting an appearance of a mammogram image for the patient's current examination using the generative adversarial network based on a mammogram image obtained from a prior examination of the patient labeled with the first type of breast density classification.

Other forms of the embodiment of the method described above are in a system and in a computer program product.

The foregoing has outlined rather generally the features and technical advantages of one or more embodiments of the present invention in order that the detailed description of the present invention that follows may be better understood. Additional features and advantages of the present invention will be described hereinafter which may form the subject of the claims of the present invention.

BRIEF DESCRIPTION OF THE DRAWINGS

A better understanding of the present invention can be obtained when the following detailed description is considered in conjunction with the following drawings, in which.

DETAILED DESCRIPTION

Figure 1:
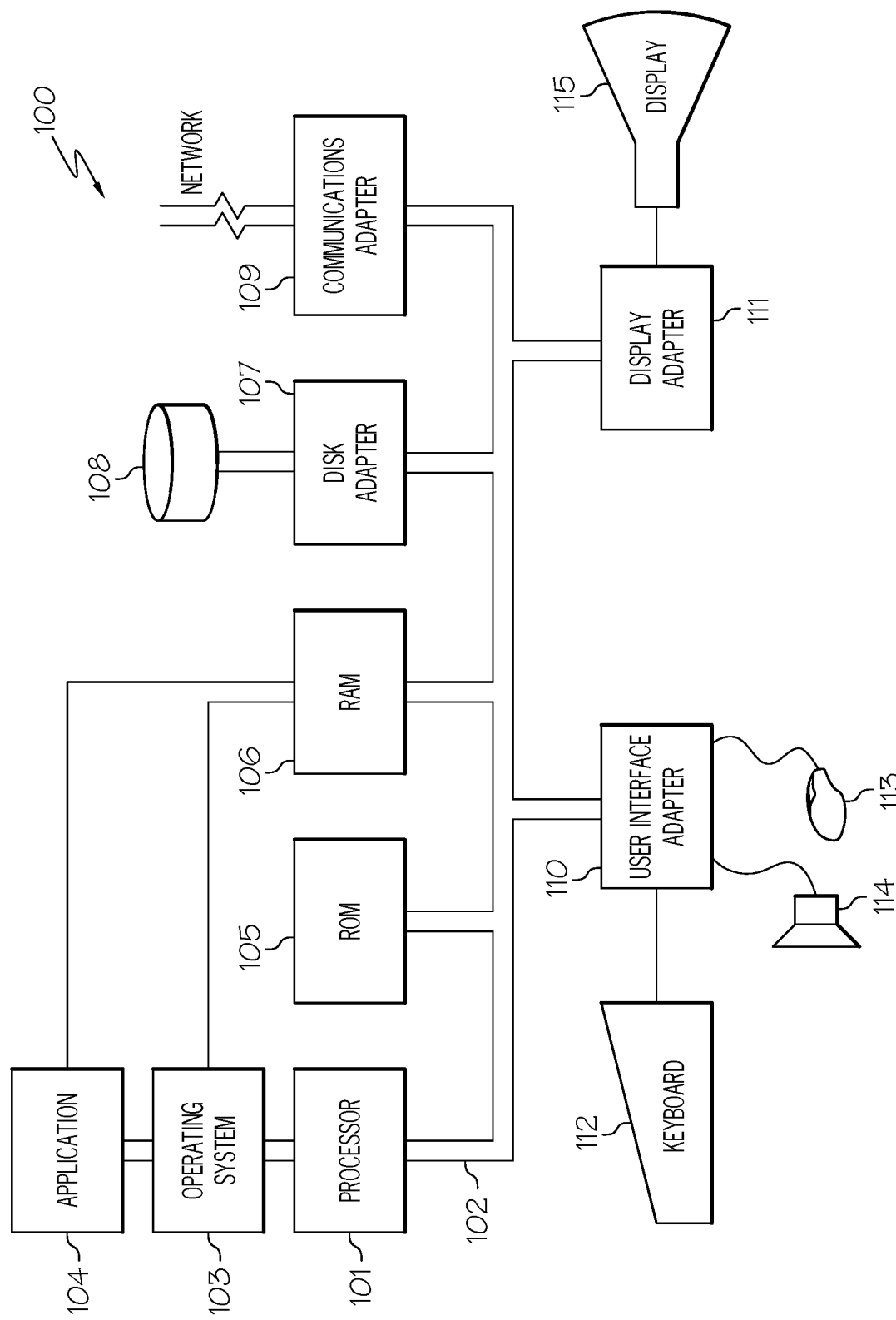
FIG. 1 illustrates an embodiment of the present invention of a hardware configuration of a computing device which is representative of a hardware environment for practicing the present invention.

The present invention comprises a method, system and computer program product for determining changes in breast density in mammogram images. In one embodiment of the present invention, a set of mammogram images labeled by users (e.g., experts) with a second type of breast density classification (e.g., BI-RADS fourth edition density labels) is received by a computing device. Such a set of mammogram images includes mammogram images for both prior and current examinations for different patients with various patient demographics (e.g., age, body mass index, etc.). The computing device then assigns the first type of breast density classification labels (e.g., BI-RADS fifth edition density labels) to the mammogram images labeled under the second type of breast density classification using a convolutional neural network. A generative adversarial network is trained to predict an appearance of a mammogram image for a patient's current examination based on the received set of mammogram images assigned labels of the first type of breast density classification. The computing device then predicts the appearance of a mammogram image for a patient's current examination using the generative adversarial network based on a mammogram image(s) obtained from the patient's prior examination labeled with the first type of breast density classification and a feature vector representing demographic characteristics of the patient. The predicted mammogram image includes a score(s) for a first type of breast density classification. The predicted appearance of the mammogram image for the patient's current examination is then compared with an actual mammogram image for the patient's current examination, where the actual mammogram image includes a score(s) for a first type of breast density classification (e.g., BI-RADS fifth edition density labels). If such scores differ, then an indication is generated that indicates that the difference is due to the subjective assessment by different physicians or changes in the standards of density classification in response to such scores differing within a threshold amount of difference. If, however, the difference between the labeled scores for the predicated and actual mammogram images is not within a threshold amount of difference, then an indication is generated that requests a technician (e.g., radiologist) to analyze the labels for the patient's mammogram images for both prior and current examinations (e.g., BI-RADS fifth edition density labels) to determine if the difference in the scores is due to a real change in breast density or is due to subjective assessments by different physicians or changes in the standards of breast density classification. In this manner, the accuracy in assessing breast density from mammogram images as well as accuracy in assessing a patient's risk for breast cancer is improved.

In the following description, numerous specific details are set forth to provide a thorough understanding of the present invention. However, it will be apparent to those skilled in the art that the present invention may be practiced without such specific details. In other instances, well-known circuits have been shown in block diagram form in order not to obscure the present invention in unnecessary detail. For the most part, details considering timing considerations and the like have been omitted inasmuch as such details are not necessary to obtain a complete understanding of the present invention and are within the skills of persons of ordinary skill in the relevant art.

Referring now to the Figures in detail, FIG. 1 illustrates an embodiment of the present invention of the hardware configuration of a computing device 100 which is representative of a hardware environment for practicing the present invention. Computing device 100 may be any type of computing device (e.g., portable computing unit, Personal Digital Assistant (PDA), laptop computer, mobile device, tablet personal computer, smartphone, mobile phone, navigation device, gaming unit, desktop computer system, workstation, Internet appliance and the like) configured with the capability of standardizing and predicting breast density classifications as well as determining changes in breast density in mammogram images.

Referring to FIG. 1, computing device 100 may have a processor 101 coupled to various other components by system bus 102. An operating system 103 may run on processor 101 and provide control and coordinate the functions of the various components of FIG. 1. An application 104 in accordance with the principles of the present invention may run in conjunction with operating system 103 and provide calls to operating system 103 where the calls implement the various functions or services to be performed by application 104. Application 104 may include, for example, a program for standardizing and predicting breast density classifications as well as determining changes in breast density in mammogram images as discussed further below in connection with FIGS. 2 and 3A-3B.

Referring again to FIG. 1, read-only memory ("ROM") 105 may be coupled to system bus 102 and include a basic input/output system ("BIOS") that controls certain basic functions of computing device 100. Random access memory ("RAM") 106 and disk adapter 107 may also be coupled to system bus 102. It should be noted that software components including operating system 103 and application 104 may be loaded into RAM 106, which may be computing device's 100 main memory for execution. Disk adapter 107 may be an integrated drive electronics ("IDE") adapter that communicates with a disk unit 108, e.g., disk drive. It is noted that the program for standardizing and predicting breast density classifications as well as determining changes in breast density in mammogram images, as discussed further below in connection with FIGS. 2 and 3A-3B, may reside in disk unit 108 or in application 104.

Computing device 100 may further include a communications adapter 109 coupled to bus 102. Communications adapter 109 may interconnect bus 102 with an outside network thereby allowing computing device 100 to communicate with other devices.

I/O devices may also be connected to computing device 100 via a user interface adapter 110 and a display adapter 111. Keyboard 112, mouse 113 and speaker 114 may all be interconnected to bus 102 through user interface adapter 110. A display monitor 115 may be connected to system bus 102 by display adapter 111. In this manner, a user is capable of inputting to computing device 100 through keyboard 112 or mouse 113 and receiving output from computing device 100 via display 115 or speaker 114. Other input mechanisms may be used to input data to computing device 100 that are not shown in FIG. 1, such as display 115 having touchscreen capability and keyboard 112 being a virtual keyboard. Computing device 100 of FIG. 1 is not to be limited in scope to the elements depicted in FIG. 1 and may include fewer or additional elements than depicted in FIG. 1.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As stated in the Background section, mammogram images are analyzed to determine breast density since women whose breasts appear dense on the mammogram image have a higher risk for breast cancer, including some aggressive breast cancers. One of the strongest known risk factors for breast cancer is high breast density—that is, relatively little fat in the breast and more connective and glandular tissue, as seen on the mammogram image. Breast density in mammogram images is currently analyzed by a radiologist using a standard referred to as the Breast Imaging-Reporting and Data System (BI-RADS) standard. BI-RADS is a quality assurance tool designed to standardize reporting and is used by medical professionals to communicate a patient's risk of developing breast cancer. BI-RADS includes standardized numerical codes that are typically assigned by a radiologist after interpreting a mammogram image, which are included in a report (breast imaging report) concerning the patient's risk of developing breast cancer. There have been several updates to the BI-RADS standard. For example, the BI-RADS is currently on its fifth edition, which was released in February of 2014. Some of the changes from the fourth edition to the fifth edition include the categorization of breast density. In the fourth edition of the BI-RADS standard, breast density is characterized on the basis of the percentile of glandular tissue within each breast (<25%, 25%-50%, 51%-75%, or >75%). Breast density characterization in the fifth edition is purely subjective, with elimination of the percentiles. The fifth edition reverts to the original description of breast density that was used in the first few editions. The four category descriptors are phrased the same in the fourth and fifth editions: almost entirely fatty, scattered areas of fibroglandular density, heterogeneously dense, and extremely dense. As a result of the continuous changes to the BI-RADS standard, radiologist reports may include different breast density characterizations. Additionally, along with changes to the BI-RADS standard, the radiologist report concerning the patient's risk of developing breast cancer may provide descriptions of breast density that do not follow any of the BI-RADS standards. As a result of the continuous changes to the BI-RADS standard as well as radiologist reports that provide descriptions of breast density that may not follow any of the BI-RADS standards, it may be difficult to assess the patient's risk for breast cancer based on the patient's medical history. Additionally, there may be difficultly in evaluating the changes in breast density for a patient over time.

The embodiments of the present invention provide a means for standardizing breast density assessments, such as across different hospitals who may be using different BI-RADS editions or their own protocols in assessing the breast density from mammogram images as discussed further below in connection with FIG. 2. By standardizing the breast density assessments, the present invention will reduce the inconsistencies in breast density characterizations thereby improving the evaluation of a patient's risk for breast cancer based on the patient's medical history as well as improving the ability for evaluating the changes in breast density for a patient over time. For example, such standardization may be utilized by the embodiments of the present invention to determine changes in breast density in mammogram images. For instance, an appearance of a mammogram image for a current examination is predicted, which is compared against an actual mammogram image for the current examination to determine whether there are changes in breast density, and if so, if such differences can be attributed to subjective assessments by physicians or changes in the BI-RADS standard or due to actual changes in breast density, as discussed further below in connection with FIGS. 3A-3B.

Figure 2:
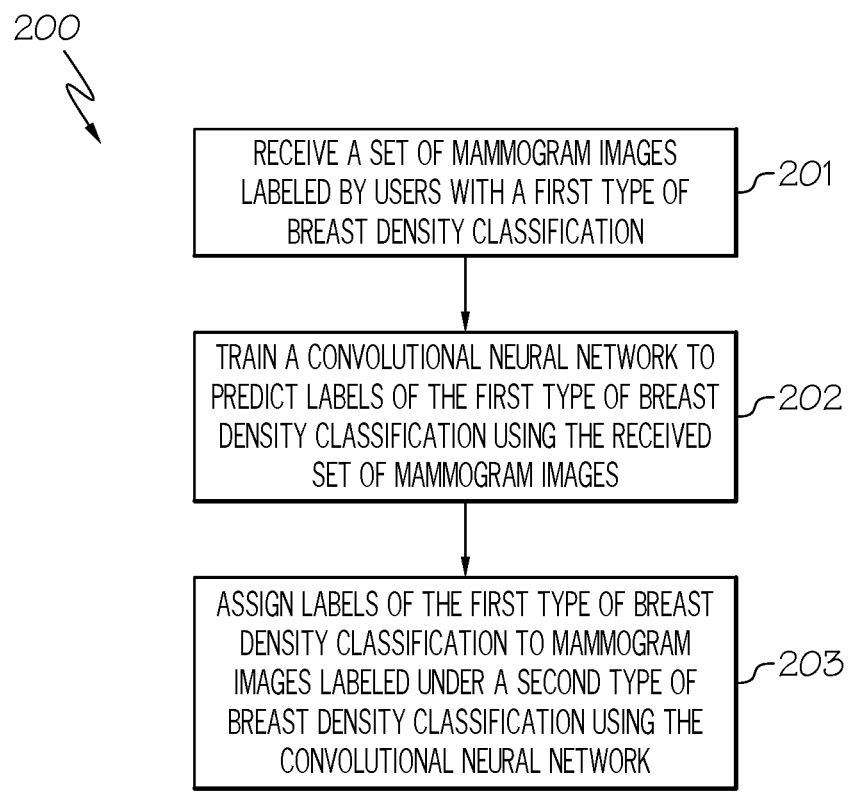
FIG. 2 is a flowchart of a method for assigning a particular breast density classification label to mammogram images labeled under a different type of breast density classification in accordance with an embodiment of the present invention.
Figure 3A:
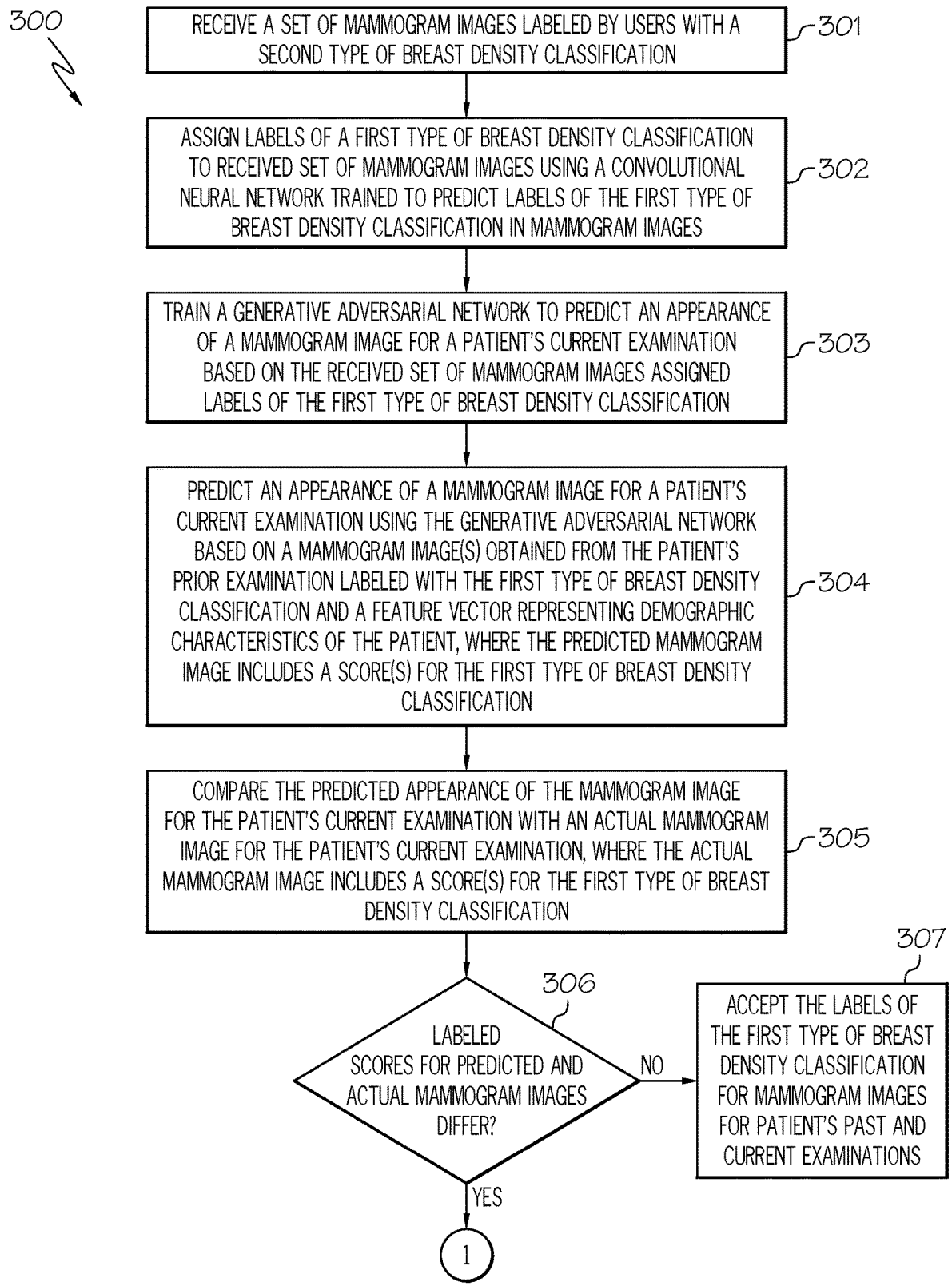
FIGS. 3A-3B are a flowchart of a method for determining changes in breast density in mammogram images in accordance with an embodiment of the present invention.
Figure 3B:
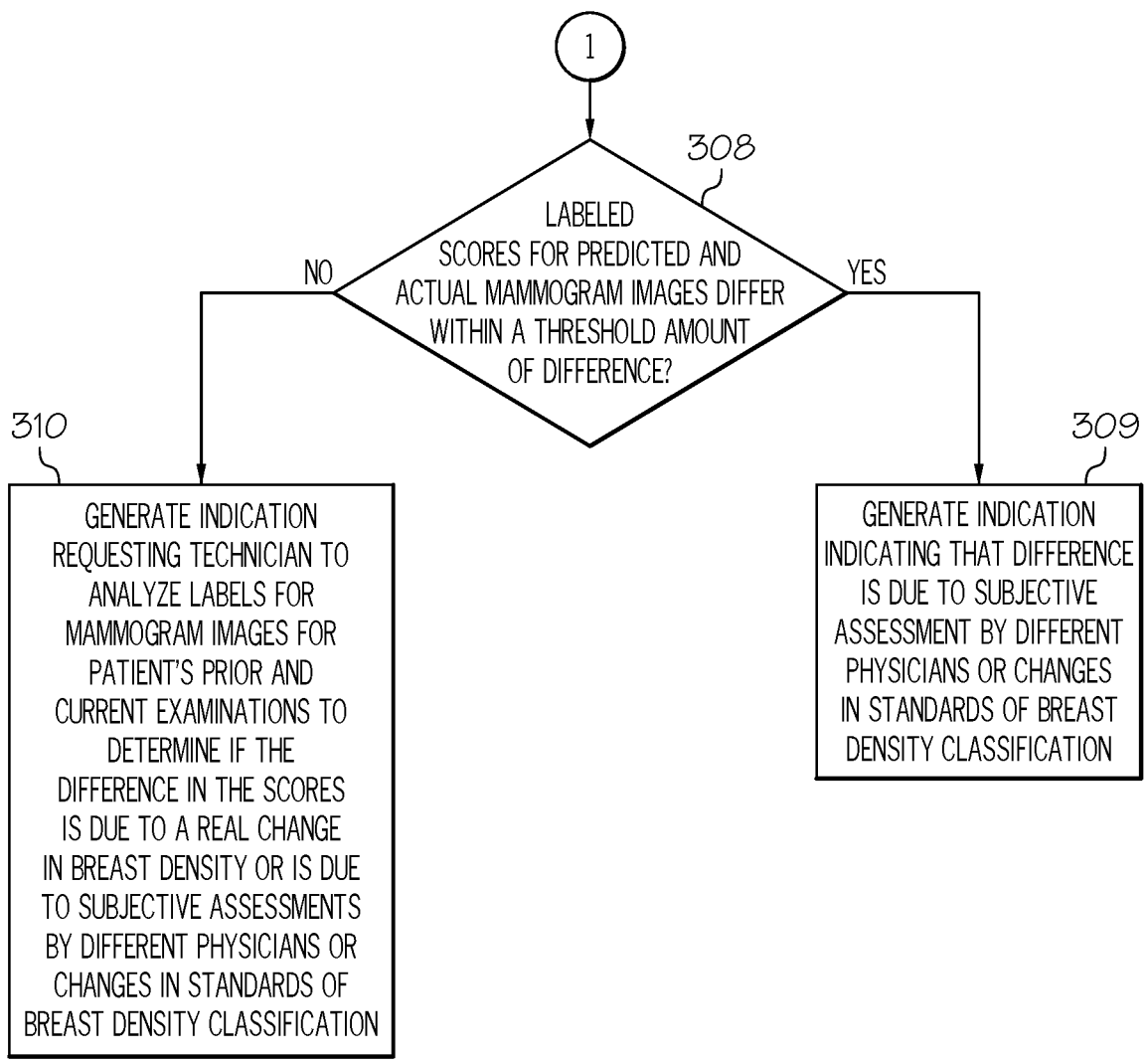

FIG. 2 is a flowchart of a method for assigning a particular breast density classification label (e.g., BI-RADS fifth edition density labels) to mammogram images labeled under a different type of breast density classification (e.g., BI-RADS fourth edition density labels). FIGS. 3A-3B are a flowchart of a method for determining changes in breast density in mammogram images.

As stated above, FIG. 2 is a flowchart of a method 200 for assigning a particular breast density classification label (e.g., BI-RADS fifth edition density labels) to mammogram images labeled under a different type of breast density classification (e.g., BI-RADS fourth edition density labels) in accordance with an embodiment of the present invention.

Referring to FIG. 2, in conjunction with FIG. 1, in step 201, computing device 100 receives a set of mammogram images labeled by users (e.g., experts) with a first type of breast density classification (e.g., BI-RADS fifth edition density labels). Such a set of mammogram images includes images with a wide range of acquisition dates, patient demographics and device manufacturers.

In step 202, computing device 100 trains a convolutional neural network to predict labels of the first type of breast density classification (e.g., BI-RADS fifth edition density labels) using the received set of mammogram images. A convolutional neural network is a class of deep, feed-forward artificial neural network, applied to analyzing visual imagery. In one embodiment, the convolutional neural network is trained as a classifier using the TensorFlow® deep learning framework developed by Google®.

In one embodiment, the convolutional neural network applies a series of filters to the raw pixel data of an image to extract and learn higher-level features, which a model can then use for classification. In one embodiment, the convolutional neural network contains three components, the convolutional layers, pooling layers and the dense layers.

The convolutional layers apply a specified number of convolution filters to the image. For each sub-region, the layer performs a set of mathematical operations to produce a single value in the output feature map. Convolutional layers may then apply a ReLU activation function to the output to introduce nonlinearities into the model.

The pooling layers downsample the image data extracted by the convolutional layers to reduce the dimensionality of the feature map in order to decrease processing time. In one embodiment, the pooling algorithm utilized is the max pooling, which extracts sub-regions of the feature map (e.g., 2×2-pixel tiles), keeps their maximum value, and discards all other values.

The dense (fully connected) layers perform classification on the features extracted by the convolutional layers and downsampled by the pooling layers. In a dense layer, every node in the layer is connected to every node in the preceding layer.

In one embodiment, the convolutional neural network is composed of a stack of convolutional modules that perform feature extraction. Each module consists of a convolutional layer followed by a pooling layer. The last convolutional module is followed by one or more dense layers that perform classification. The final dense layer in a convolutional neural network contains a single node for each target class in the model (all the possible classes the model may predict), with a softmax activation function (the softmax function is a generalization of the logistic function that "squashes" a K-dimensional vector z of arbitrary real values to a K-dimensional vector $\sigma(z)$ of real values, where each entry is in the range (0, 1), and all the entries add up to 1) to generate a value between 0-1 for each node (the sum of all these softmax values is equal to 1). The softmax values can be interpreted for a given image as relative measurements of how likely it is that the image falls into each target class.

In step 203, computing device 100 assigns the first type of breast density classification labels (e.g., BI-RADS fifth edition density labels) to images labeled under a second type of breast density classification (e.g., BI-RADS fourth edition density labels) using the convolutional neural network.

In this manner, embodiments of the present invention utilize a convolutional neural network to standardize breast density assessments, such as across different hospitals who may be using different BI-RADS editions or their own protocols in assessing the breast density from mammogram images. By standardizing the breast density assessments, the present invention will reduce the inconsistencies in breast density characterizations thereby improving the evaluation of a patient's risk for breast cancer based on the patient's medical history as well as improving the ability for evaluating the changes in breast density for a patient over time.

While the foregoing discusses the example of assigning the BI-RADS fifth edition density labels to mammogram images labeled under the BI-RADS fourth edition, the principles of the present invention may include assigning any type of breast density labels to mammogram images labeled under a different type of breast density classification. For example, the present invention may be utilized to assign the BI-RADS fifth edition density labels to mammogram images labeled under the BI-RADS third edition. In such an embodiment, the convolutional neural network can be trained to predict the BI-RADS fifth edition density labels from mammogram images labeled under the BI-RADS third edition.

Embodiments of the present invention further utilize a second model (in addition to the deep learning model discussed above) to predict the appearance of a mammogram image for a patient's current examination based on the patient's previous examination images to determine changes in breast density in mammogram images as discussed below in connection with FIGS. 3A-3B.

FIGS. 3A-3B are a flowchart of a method 300 for determining changes in breast density in mammogram images in accordance with an embodiment of the present invention.

Referring to FIG. 3A, in conjunction with FIGS. 1-2, in step 301, computing device 100 receives a set of mammogram images labeled by users (e.g., experts) with a second type of breast density classification (e.g., BI-RADS fourth edition density labels). Such a set of mammogram images includes mammogram images for both prior and current examinations for different patients with various patient demographics (e.g., age, body mass index, etc.).

In step 302, computing device 100 assigns labels of a first type of breast density classification labels (e.g., BI-RADS fifth edition density labels) to the received set of mammogram images using the convolutional neural network of FIG. 2 (deep learning method of FIG. 2) trained to predict labels of the first type of breast density classification in mammogram images.

In step 303, computing device 100 trains a generative adversarial network to predict an appearance of a mammogram image for a patient's current examination based on the received set of mammogram images assigned labels of the first type of breast density classification. A generative adversarial network is a class of artificial intelligence algorithms used in unsupervised machine learning and implemented by a system of two neural networks contesting with each other in a zero-sum game framework.

In one embodiment, the resolution of the predicted mammogram image and the received mammogram images are matched so that they both have the highest resolution available. In such a scenario, the image with a lower resolution may be reconstructed to have the matching higher resolution, such as by using super resolution reconstruction (SRR).

In one embodiment, a generative adversarial network is trained to predict an appearance of a mammogram image using a framework based on the following idea: the generator neural network aims to produce realistic examples able to deceive the discriminator which aims to discern between original and generated ones (a "critic"). The two networks form an adversarial relationship and gradually improve one another through competition, such as two opponents in a zero-sum game.

In one embodiment, training these models may require reaching a Nash equilibrium, which may be a challenging task. As a result, training can be unstable, susceptible to mode collapse and gradient saturations. Consequently, in one embodiment, training is started at low resolution before gradually increasing it as more layers are phased in. That is, new layers are gradually added to the generator and discriminator networks. The generator first learns to synthesize the high-level structure and low frequency details of the image distribution before gradually shifting its attention to finer details in higher scales. The fact that the generator does not need to learn all scales at once leads to increased training stability. Progressive training also reduces training time since most of the iterations are done at lower resolutions where the network sizes are small. Hence, the result of starting the training at low resolution before gradually increasing it as more layers are phased in is to increase training stability at high resolutions as well as to speed up training.

In step 304, computing device 100 predicts the appearance of a mammogram image for a patient's current examination using the generative adversarial network based on a mammogram image(s) obtained from the patient's prior examination labeled with the first type of breast density classification (e.g., BI-RADS fifth edition) and a feature vector representing demographic characteristics of the patient. That is, the generative adversarial network is seeded with a prior mammogram image(s) of the first type of breast density classification (e.g., BI-RADS fifth edition density labels) and a vector representing the patient's demographic characteristics (e.g., age, BMI). It is noted that any of the patient's mammograms from prior examinations labeled with an older standard (e.g., BI-RADS fourth edition) can be assigned labels for a newer standard (e.g., BI-RADS fourth edition) using the convolutional neural network discussed in connection with FIG. 2.

Such information is used by the generative adversarial network as discussed above to generate an appearance of a mammogram image for a patient's current examination.

In one embodiment, the predicted mammogram image includes a score(s) for the first type of breast density classification (e.g., BI-RADS fifth edition).

In one embodiment, the resolution of the predicted mammogram image and the prior mammogram image(s) are matched so that they both have the highest resolution available. In such a scenario, the image with a lower resolution may be reconstructed to have the matching higher resolution, such as by using super resolution reconstruction (SRR).

In step 305, computing device 100 compares the predicted appearance of the mammogram image for the patient's current examination with an actual mammogram image for the patient's current examination labeled with the first type of breast density classification, where the actual mammogram image includes a score(s) for the first type of breast density classification (e.g., BI-RADS fifth edition). In one embodiment, a technician, such as a radiologist, provides computing device 100 with the actual mammogram image for the patient's current examination that is labeled with the first type of breast density classification, where such labels include scores for the first type of breast density classification.

In step 306, a determination is made by computing device 100 as to whether the scores (value of the scores) for the predicted and mammogram images differ.

If such scores do not differ (i.e., if the values of the scores do not differ), then, in step 307, computing device 100 accepts the labels of the first type of breast density classification for the mammogram images for the past and current examinations of the patient. As discussed above, the mammogram images for the past and/or current examinations of the patient may have previously been in a different standard than the first type of breast density classification. As a result, the convolutional neural network of the present invention was utilized to predict labels for these mammogram images of the first type of breast density classification.

Referring now to FIG. 3B, in conjunction with FIGS. 1-2, if, however, such scores differ, then, in step 308, a determination is made by computing device 100 as to whether the difference in the value of the scores is within a threshold amount of difference, which may be user-selected.

If the difference in value between the labeled scores for the predicated and actual mammogram images is within a threshold amount of difference, then, in step 309, computing device 100 generates an indication (e.g., message displayed on display 115) indicating that the difference is due to the subjective assessment by different physicians or changes in the standards of breast density classification.

If, however, the difference in value between the labeled scores for the predicated and actual mammogram images is not within a threshold amount of difference, then, in step 310, computing device 100 generates an indication (e.g., message displayed on display 115) requesting the technician (e.g., radiologist) to analyze the labels for the patient's mammogram images for both prior and current examinations (labeled with the first type of breast density classification) to determine if the difference in the scores is due to a real change in breast density or is due to subjective assessments by different physicians or changes in the standards of breast density classification.

In this manner, embodiments of the present invention determine changes in breast density in mammogram images by utilizing a generative adversarial network to predict the appearance of a mammogram image for the patient's current examination, which is compared against an actual mammogram image of the patient's current examination. Based on the degree of difference in the labeled scores for the predicted and actual mammogram images, such a determination may determine whether the difference is due to subjective assessments by different physicians or changes in the standards of breast density classification or requires further analysis by a technician (e.g., radiologist) to determine if the change is due to an actual change in breast density. As a result, embodiments of the present invention improve the accuracy in assessing breast density from mammogram images as well as improve the assessment of a patient's risk for breast cancer.

Furthermore, the present invention improves the technology or technical field involving mammography. As discussed above, as a result of the continuous changes to the BI-RADS standard as well as radiologist reports that provide descriptions of breast density that may not follow any of the BI-RADS standards, it may be difficult to assess the patient's risk for breast cancer based on the patient's medical history. Additionally, there may be difficultly in evaluating the changes in breast density for a patient over time.

The present invention improves such technology by standardizing breast density assessments, such as across different hospitals who may be using different BI-RADS editions or their own protocols in assessing the breast density from mammogram images. By standardizing the breast density assessments, the present invention will reduce the inconsistencies in breast density characterizations thereby improving the evaluation of a patient's risk for breast cancer based on the patient's medical history as well as improving the ability for evaluating the changes in breast density for a patient over time.

For example, such standardization may be utilized by the embodiments of the present invention to determine changes in breast density in mammogram images. For instance, an appearance of a mammogram image for a current examination is predicted, which is compared against an actual mammogram image for the current examination to determine whether there are changes in breast density, and if so, if such differences can be attributed to subjective assessments by physicians or changes in the BI-RADS standard or due to actual changes in breast density. As a result, embodiments of the present invention improve the accuracy in assessing breast density from mammogram images as well as improve the assessment of a patient's risk for breast cancer.

The technical solution provided by the present invention cannot be performed in the human mind or by a human using a pen and paper. That is, the technical solution provided by the present invention could not be accomplished in the human mind or by a human using a pen and paper in any reasonable amount of time and with any reasonable expectation of accuracy without the use of a computer.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for determining changes in breast density in mammogram images, the method comprising:
   receiving a set of mammogram images labeled by users with a second type of breast density classification, wherein said mammogram images comprise mammogram images of patients obtained from both prior and current examinations;
   assigning labels of a first type of breast density classification to said received set of mammogram images using a convolutional neural network trained to predict labels of said first type of breast density classification in mammogram images;
   training a generative adversarial network to predict an appearance of a mammogram image for a patient's current examination based on said received set of mammogram images assigned labels of said first type of breast density classification; and
   predicting an appearance of a mammogram image for said patient's current examination using said generative adversarial network based on a mammogram image obtained from a prior examination of said patient labeled with said first type of breast density classification.

2. The method as recited in claim 1 further comprising:
predicting said appearance of said mammogram image for said patient's current examination using said generative adversarial network based on said mammogram image obtained from said patient's prior examination and a feature vector representing demographic characteristics of said patient.

3. The method as recited in claim 1 further comprising:
comparing said predicted appearance of said mammogram image for said patient's current examination with an actual mammogram image for said patient's current examination labeled with said first type of breast density classification.

4. The method as recited in claim 3, wherein said predicted mammogram image is assigned a score for said first type of breast density classification, wherein said actual mammogram image is assigned a score for said first type of breast density classification.

5. The method as recited in claim 4 further comprising:
accepting labels of said first type of breast density classification in mammogram images of said patient for past and current examinations in response to said score assigned to said predicted mammogram image matching said score assigned to said actual mammogram image.

6. The method as recited in claim 4 further comprising:
generating an indication indicating that a difference in value between said score assigned to said predicted mammogram image and said score assigned to said actual mammogram image is due to subjective assessments by different physicians or changes in standards of density classification in response to said score assigned to said predicted mammogram image differing from said score assigned to said actual mammogram image within a threshold amount of difference.

7. The method as recited in claim 4 further comprising:
generating an indication requesting a technician to analyze labels for mammogram images for said patient's prior and current examinations labeled with said first type of breast density classification to determine if a difference in value between scores assigned to said predicted mammogram image and said actual mammogram image is due to subjective assessments by different physicians or changes in standards of density classification or is due to a real change in breast density in response to said score assigned to said predicted mammogram image differing from said score assigned to said actual mammogram image not within a threshold amount of difference.

8. The method as recited in claim 1, wherein said first and second types of breast density classifications comprise different standards of a Breast Imaging Reporting and Data System (BI-RADS) breast density classification.

9. The method as recited in claim 1, wherein said first type of breast density classification comprises BI-RADS fifth edition density labels, wherein said second type of breast density classification comprises BI-RADS fourth edition density labels.

10. A computer program product for determining changes in breast density in mammogram images, the computer program product comprising a computer readable storage medium having program code embodied therewith, the program code comprising the programming instructions for:
receiving a set of mammogram images labeled by users with a second type of density classification, wherein said mammogram images comprise mammogram images of patients obtained from both prior and current examinations;
assigning labels of a first type of breast density classification to said received set of mammogram images using a convolutional neural network trained to predict labels of said first type of breast density classification in mammogram images;
training a generative adversarial network to predict an appearance of a mammogram image for a patient's current examination based on said received set of mammogram images assigned labels of said first type of breast density classification; and
predicting an appearance of a mammogram image for said patient's current examination using said generative adversarial network based on a mammogram image obtained from a prior examination of said patient labeled with said first type of breast density classification.

11. The computer program product as recited in claim 10, wherein the program code further comprises the programming instructions for:
predicting said appearance of said mammogram image for said patient's current examination using said generative adversarial network based on said mammogram image obtained from said patient's prior examination and a feature vector representing demographic characteristics of said patient.

12. The computer program product as recited in claim 10, wherein the program code further comprises the programming instructions for:
comparing said predicted appearance of said mammogram image for said patient's current examination with an actual appearance of a mammogram image for said patient's current examination labeled with said first type of breast density classification.

13. The computer program product as recited in claim 12, wherein said predicted mammogram image is assigned a score for said first type of breast density classification, wherein said actual mammogram image is assigned a score for said first type of breast density classification.

14. The computer program product as recited in claim 13, wherein the program code further comprises the programming instructions for:
accepting labels of said first type of breast density classification in mammogram images of said patient for past and current examinations in response to said score assigned to said predicted mammogram image matching said score assigned to said actual mammogram image.

15. The computer program product as recited in claim 13, wherein the program code further comprises the programming instructions for:
generating an indication indicating that a difference in value between said score assigned to said predicted mammogram image and said score assigned to said actual mammogram image is due to subjective assessments by different physicians or changes in standards of density classification in response to said score assigned to said predicted mammogram image differing from said score assigned to said actual mammogram image within a threshold amount of difference.

16. The computer program product as recited in claim 13, wherein the program code further comprises the programming instructions for:
generating an indication requesting a technician to analyze labels for mammogram images for said patient's prior and current examinations to determine if a difference in value between scores assigned to said predicted mammogram image and said actual mammogram image is due to subjective assessments by different physicians or changes in standards of density classification or is due to a real change in breast density in response to said score assigned to said predicted mammogram image differing from said score assigned to said actual mammogram image not within a threshold amount of difference.

17. The computer program product as recited in claim 10, wherein said first and second types of breast density classifications comprise different standards of a Breast Imaging Reporting and Data System (BI-RADS) breast density classification.

18. The computer program product as recited in claim 10, wherein said first type of breast density classification comprises BI-RADS fifth edition density labels, wherein said second type of breast density classification comprises BI-RADS fourth edition density labels.

\* \* \* \* \*

UNITED STATES PATENT AND TRADEMARK OFFICE
CERTIFICATE OF CORRECTION

| | |
|---|---|
| PATENT NO. | : 10,898,149 B2 |
| APPLICATION NO. | : 16/216052 |
| DATED | : January 26, 2021 |
| INVENTOR(S) | : Sun Young Park et al. |

It is certified that error appears in the above-identified patent and that said Letters Patent is hereby corrected as shown below:

On the Title Page

Item (72), Replace the first name of the second inventor "Dusty" with the first and middle name of --Dustin Michael--.

Signed and Sealed this
Seventh Day of June, 2022

Katherine Kelly Vidal
*Director of the United States Patent and Trademark Office*